United States Patent [19]

Mookherjee et al.

[11] 4,211,242
[45] Jul. 8, 1980

[54] COMPOSITION OF MATTER COMPRISING MORE THAN 50% TRANS, TRANS-Δ-DAMASCONE FOR AUGMENTING OR ENHANCING THE AROMA AND TASTE OF A SMOKING TOBACCO

[75] Inventors: Braja D. Mookherjee, Holmdel; Robert W. Trenkle, Bricktown; Richard A. Wilson, Westfield; Frederick L. Schmitt, Holmdel; Manfred H. Vock, Locust; Edward J. Granda, Englishtown; Joacquin Vinals, Red Bank, all of N.J.; Jacob Kiwala, Brooklyn, N.Y.; William L. Schreiber, Jackson, N.J.

[73] Assignee: International Flavors & Fragrances Inc., New York, N.Y.

[21] Appl. No.: 851,727

[22] Filed: Nov. 15, 1977

[51] Int. Cl.² .................................................. A24B 3/12
[52] U.S. Cl. ................................... 131/17 R; 131/144
[58] Field of Search ................. 131/17 R, 144, 15 R, 131/2; 260/586 R; 426/538; 252/522

[56] References Cited

U.S. PATENT DOCUMENTS 3,887,625   6/1975   Shulte-Elte ............... 131/17 R UX

*Primary Examiner*—V. Millin
*Attorney, Agent, or Firm*—Arthur L. Liberman; Franklun D. Wolffe

[57] ABSTRACT

Described is a process for augmenting or enhancing the aroma and taste of a smoking tobacco comprising adding to said smoking tobacco an organoleptic property modifying quantity of a composition of matter comprising more than 50% trans,trans-Δ-damascone and in addition a process for augmenting or enhancing the aroma and taste of a smoking tobacco comprising adding to said smoking tobacco in an organoleptic property modifying quantity a product produced according to the process of (i) reacting 1-alpha-acetyl-2-alpha,6,6-trimethyl-3-cyclohexene with strong base in aqueous ethanol at reflux thereby producing 1-alpha-acetyl-2-beta,6,6-trimethyl-3-cyclohexene; (ii) reacting the 1-alpha-acetyl-2-beta,6,6-trimethyl-3-cyclohexene with n-methyl aniline Grignard thereby forming a first organometallic compound; (iii) reacting said first organometallic compound with acetaldehyde thereby forming a second organometallic compound; (iv) reacting said second organometallic compound with acid in order to hydrolyze said second organometallic compound thereby forming a hydroxy ketone having the structure:

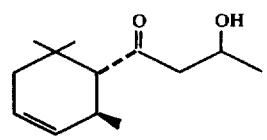

in admixture with other compounds; (v) dehydrating said hydroxy ketone in admixture with other compounds thereby forming a mixture having a major proportion of trans, trans-Δ-damascone having the structure:

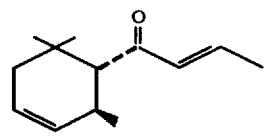

in admixture with cis, trans-Δ-damascone having the structure:

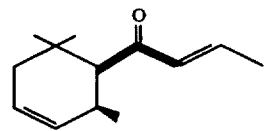

and in admixture with other compounds; and in addition smoking tobacco products containing same.

5 Claims, 4 Drawing Figures

NMR SPECTRUM FOR EXAMPLE I, CIS,TRANS ISOMER

IR SPECTRUM FOR EXAMPLE II, TRANS, TRANS, TRANS ISOMER, FRACTION 6.

COMPOSITION OF MATTER COMPRISING MORE THAN 50% TRANS, TRANS-Δ-DAMASCONE FOR AUGMENTING OR ENHANCING THE AROMA AND TASTE OF A SMOKING TOBACCO

BACKGROUND OF THE INVENTION

The present invention provides the compound trans, trans-Δ-damascone having the structure:

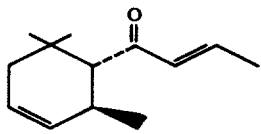

and mixtures containing a high proportion of trans, trans-Δ-damascone (more than 50%) and low proportion of cis, trans-Δ-damascone having the structure:

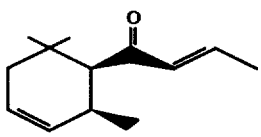

and a straightforward, economical process directed towards synthesizing trans, trans-Δ-damascone and mixtures containing a high proportion of trans, trans-Δ-damascone by means of the following reaction sequence:

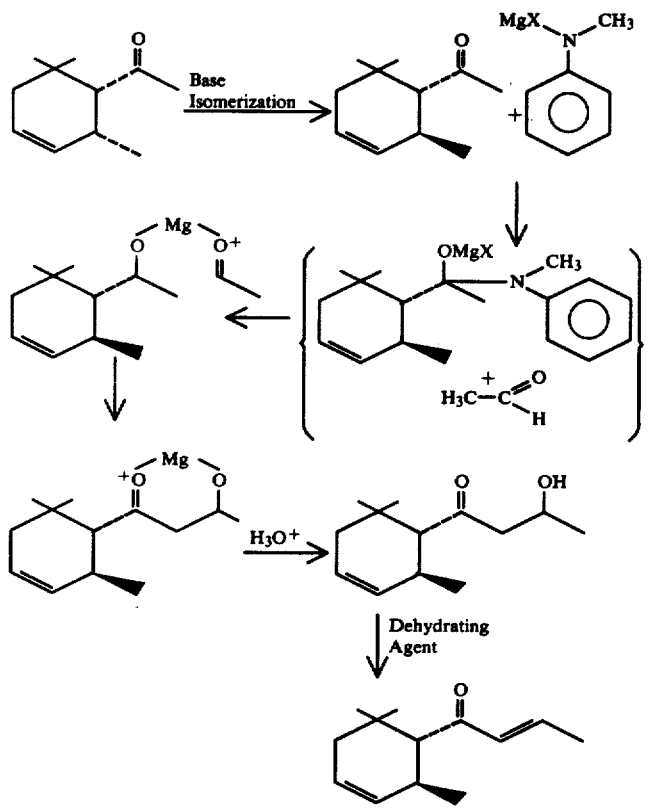

wherein X is chloro or bromo and utilization of trans, trans-Δ-damascone and mixtures containing a high proportion of trans, trans-Δ-damascone and low proportion of cis, trans-Δ-damascone for their organoleptic properties in perfumes, perfumed articles, foodstuffs, foodstuff flavoring compositions, chewing gums, toothpastes, medicinal products, tobaccos, tobacco flavoring compositions, substitute tobaccos and substitute tobacco flavoring compositions.

In the perfumery art there is a considerable need for substituents having rose, berry, apple, green and sweet floral notes. Floral, musty, hay-tea-like, sweet and fruity notes are desirable in tobacco flavoring compositions and substitute tobacco flavoring compositions. Specifically described herein are materials having such an organoleptic profile but which do not discolor with age. Such fragrance materials have a wide utilization in the presence of these perfume compounds. A limited amount of such materials that give rise to these properties is available from natural sources but the natural materials are subject to wide variations in quality, are expensive, and are often in critically short supply. The same holds true for the use of trans, trans-Δ-damascone or mixtures containing a high proportion of trans, trans-Δ-damascone and low proportion of cis, trans-Δ-damascone for use in tobacco or for use in tobacco substitutes.

In addition, there is a continuing search for food flavor compositions which can vary, fortify, modify, enhance, augment or otherwise improve the flavor and/or aroma of foodstuffs, medicinal products, toothpastes and chewing gums. To be satisfactory, such compositions should be stable, non-toxic and blendable with other ingredients to provide their own unique flavor and aroma nuances without detracting from the co-ingredients. Preferably, such compositions should be naturally occurring or present in natural foodstuffs so that their ingestible safety can be readily recognized. These materials should be capable of being synthesized in a simple and economical manner. The need for safe flavors in the berry fruit flavor area, especially the raspberry area, winey area, juice area (more especially, grape, tea and mimosa) is well known particularly in the ice cream and yogurt flavor areas. More specifically, there is a need for the development of non-toxic materials which can replace natural materials not readily available, having sweet, floral, damascenone-like, raspberry-like, fruity, cooked plum, grape juice-like, apple juice-like and winey aroma and flavor characteristics.

although mixtures presumed to be predominantly cis, trans-Δ-damascone with minor amounts of trans, trans-Δ-damascone have been produced by Ayyar, Cookson and Kagi as set forth in J. Chem. Soc., Perkin Trans. 1, 1975 (17) 1727–36 [title: "Synthesis of α-Damascone[trans-1-(2,6,6-Trimethylcyclohex-3-enyl)but-2-en-1-one] and β-Damascenone[trans-1-(2,6,6-Trimethylcyclohexa-1,3-dienyl)but-2-en-1-one]"]. The reaction sequence of the Ayyar synthesis of compositions presumed to be predominantly cis, trans-Δ-damascone with minor amounts of trans, trans-Δ-damascone is as follows:

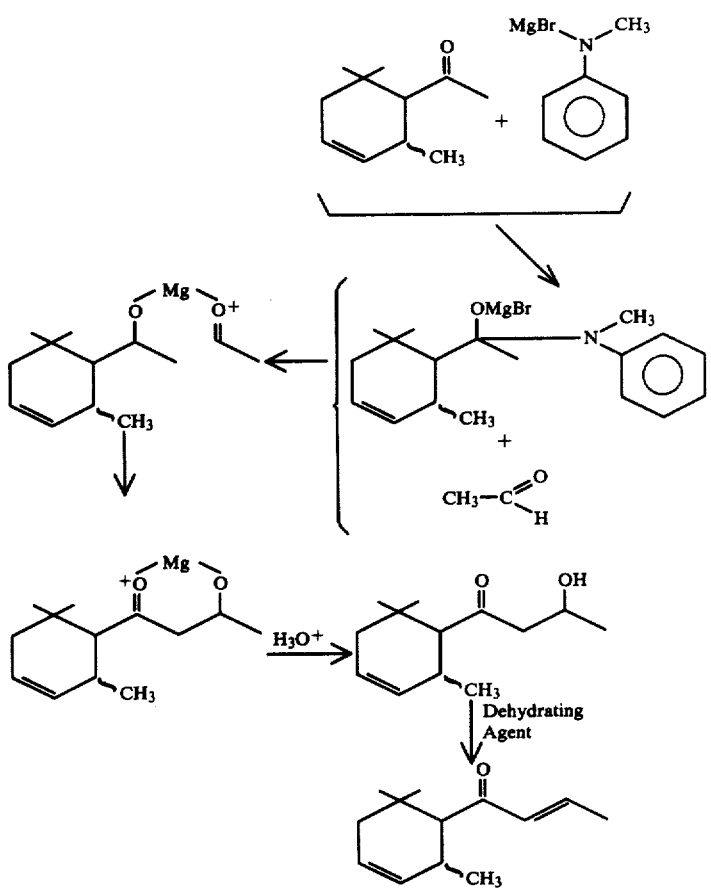

The instant invention provides the foregoing, which the prior art has heretofore failed to provide. Furthermore, nothing in the prior art shows the unexpected, unobvious and advantageous value of the compound having the structure:

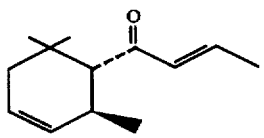

wherein the wavy line is representative of a "cis" or "trans" configuration of the methyl moiety with respect to the acetyl or oxy alkyl moiety, both of which are bonded to the cyclohexenyl moiety, the "cis" isomer presumably being the major isomer and the "trans" isomer presumably being the minor isomer in this reaction sequence.

The Ayyar, et al reference also teaches production of 3-butenoyl-4,4-dimethylcyclohexene according to the following reaction sequence:

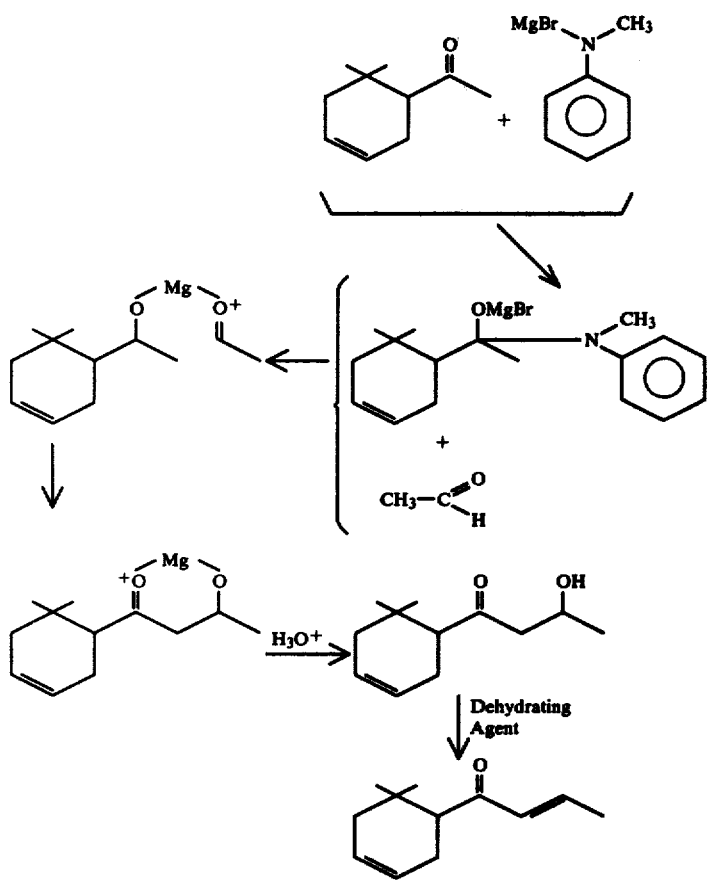

Ayyar, et al fails to teach the unexpected, unobvious significance attached to the trans, trans-Δ-damascone as discovered in the instant invention.

On the other hand, in U.S. Pat. No. 3,956,392 at column 7 and 8 it is indicated that trans, e-1-crotonyl-2,2,6-trimethylcyclohexane (totally saturated insofar as the ring moiety is concerned) has unexpected, unobvious properties over cis, e-1-crotonyl-2,2,6-trimethylcyclohexane; e-β-damascenone and e-β-damascone. It is noteworthy that whereas trans, trans-Δ-damascone of our invention has a sweet, floral, damascenone-like, raspberry, fruity, cooked plum, grape juice-like, apple juice-like, winey aroma and flavor character at 0.05 ppm with a threshold of 0.002 ppm, the corresponding cis, trans-Δ-damascone which is presumed to be the Ayyar, et al. product has a damascenone-like, fruity, raspberry-like, rosey, spiced apple-like, tobacco, winey and clove aroma character with a damascenone, fruity, raspberry, rosey, spiced apple, tobacco, winey and tea flavor character at 0.05 ppm with a threshold of 0.005 ppm. The comparison of trans, trans-Δ-damascone with cis, trans-Δ-damascone, which is presumed to be the Ayyar, et al product, is much more dramatic with respect to the perfumery properties of trans, trans-Δ-damascone as is shown in the examples set forth infra.

Swiss Pat. No. 537,352 issued on July 13, 1973 discloses 1(2-butenyl)cyclohexenes having the structure:

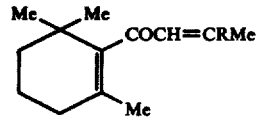

and this Swiss Patent is abstracted in Chem. Abstracts 79:104808s.

However, none of the foregoing references discloses trans, trans-Δ-damascone or mixtures containing a high percentage of trans, trans-Δ-damascone and a less than 50% quantity of cis, trans-Δ-damascone or their uses in food-stuffs, perfumes, perfumed articles, tobaccos and substituted tobaccos for their organoleptic properties.

THE INVENTION

Figure 1:
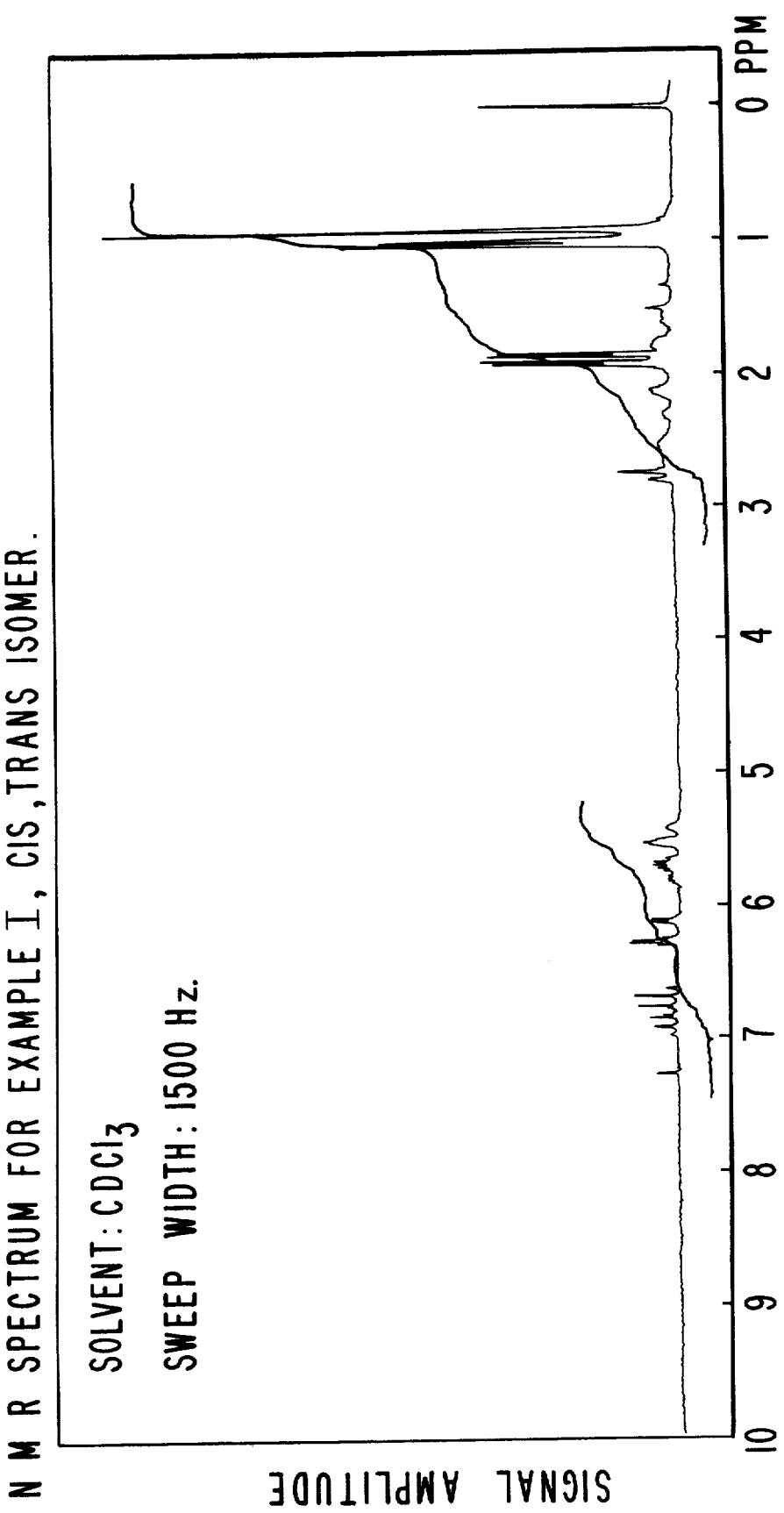
FIG. 1 represents the NMR spectrum for cis, trans-Δ-damascone produced according to the process of Example I.

The present invention provides the compound trans, trans-Δ-damascone and mixtures of trans, trans-Δ- damascone and cis, trans-Δ-damascone and a straightforward, economical process directed towards synthesizing trans, trans-Δ-damascone and mixtures of trans, trans-Δ-damascone and cis, trans-Δ-damascone wherein the percentage of trans, trans-Δ-damascone in the mixture is greater than 50%. The trans, trans-Δ-damascone of our invention has the structure:

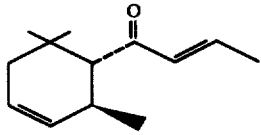

Cis, trans-Δ-damascone has the structure:

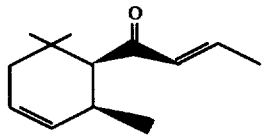

The economic straightforward process of our invention is described by the sequence:

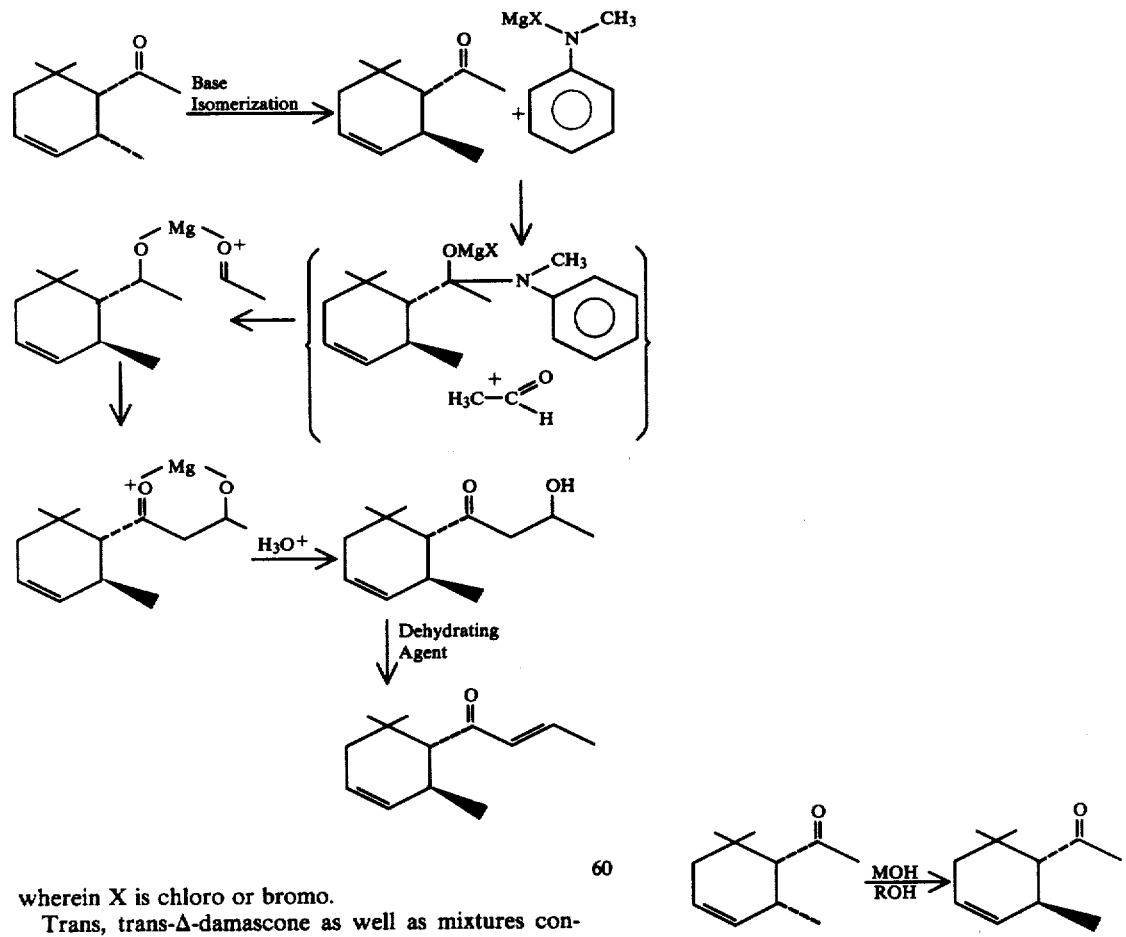

wherein X is chloro or bromo.

Trans, trans-Δ-damascone as well as mixtures containing a high proportion of trans, trans-Δ-damascone and less than 50% of cis, trans-Δ-damascone are capable of augmenting or enhancing berry fruit flavors especially raspberry flavors, wine flavors, tea flavors and juice flavors, especially grape and mimosa flavors, by imparting thereto sweet, floral, damascenone-like, raspberry-like, fruity, cooked plum, grape juice-like and apple juice-like aroma and flavor characteristics.

The compound trans, trans-Δ-damascone as well as mixtures containing a high proportion of trans, trans-Δ-damascone and less than 50% of cis, trans-Δ-damascone are also capable of modifying or enhancing the odor characteristics of perfume compositions, colognes and perfumed articles by imparting thereto sweet floral, rose, berry, apple and green fragrance notes, thus fulfilling a need in the field of perfumery.

In tobacco, tobacco flavoring compositions, substitute tobacco and substitute tobacco flavoring compositions, the compound trans, trans-Δ-damascone as well as mixtures containing more than 50% trans, trans-Δ-damascone and less than 50% cis, trans-Δ-damascone, impart floral, musty, hay-tea-like and sweet/fruity notes prior to and on smoking.

Trans, trans-Δ-damascone of our invention is produced by first preparing 1-α-acetyl-2-β, 6,6-trimethyl-3-cyclohexene by means of treatment of 1-α-acetyl-2-α, 6,6-trimethyl-3-cyclohexene with refluxing alcoholic base according to the reaction:

wherein R is lower alkyl, e.g. methyl or ethyl and M is alkali metal, e.g. sodium or potassium.

From a practical standpoint, the starting material is a composition consisting of 80% of the cis isomer of 1-acetyl-2,6,6-trimethyl-3-cyclohexene (referred to also as 1-α-acetyl-2-α, 6,6-trimethyl-3-cyclohexene) and about 16% of the trans isomer (also referred to as 1-α-acetyl-2-β, 6,6-trimethyl-3-cyclohexene). Also from a practical standpoint, the resulting product contains a minor proportion of the cis isomer (approximately 15–20%) and a major proportion of the trans isomer (approximately 80–85%).

The resulting trans isomer of 1-acetyl-2,6,6-trimethyl-3-cyclohexene, preferably the mixture containing about 80–85% of this trans isomer and about 15–20% of the cis isomer, is then reacted with an n-alkyl aniline Grignard reagent, preferably n-methyl aniline Grignard, such as n-methyl aniline magnesium chloride or n-methyl aniline magnesium bromide. Accordingly, the reaction is illustrated as follows:

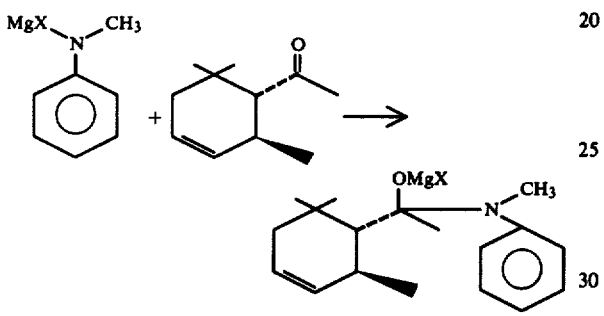

The resulting Grignard complex is then reacted with acetaldehyde thereby forming a second organo-magnesium compound according to the reaction:

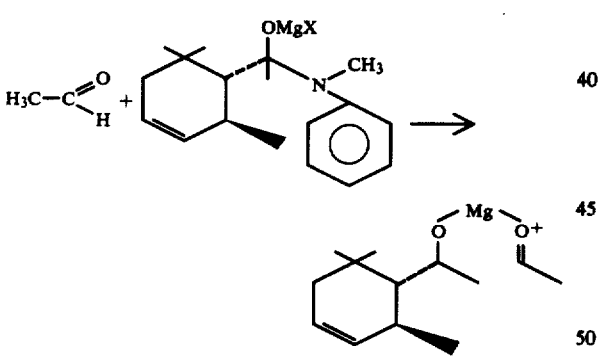

The second organo-magnesium compound rearranges itself to form a third organo-magnesium compound according to the reaction:

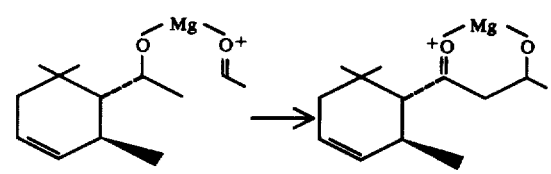

This third organo-magnesium compound is then hydrolyzed in the presence of acid, preferably mineral acid to form the desired 3-α-5,5-trimethyl-4-β(3-hydroxy-1-butanoyl)-cyclohexene according to the reaction:

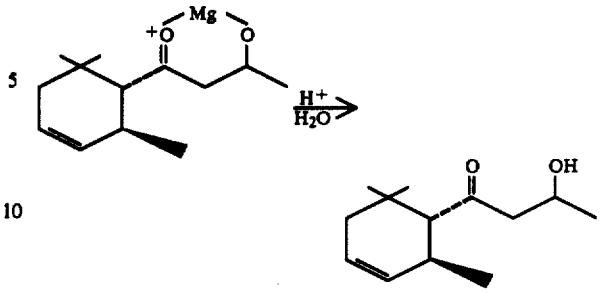

The resulting product is then dehydrated using standard dehydrating means such as paratoluenesulfonic acid thereby producing the desired trans, trans-Δ-damascone according to the reaction:

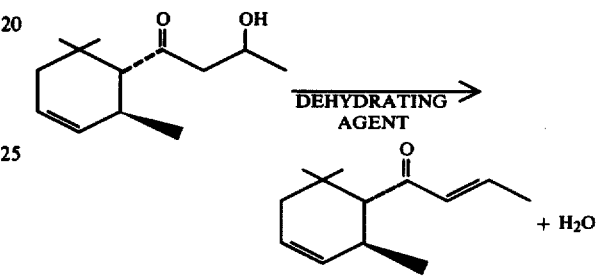

From a practical and economical standpoint, the reaction product is used as is for its organoleptic properties and this reaction product contains 80–85% trans, trans-Δ-damascone and 15–20% cis, trans-Δ-damascone having the structure:

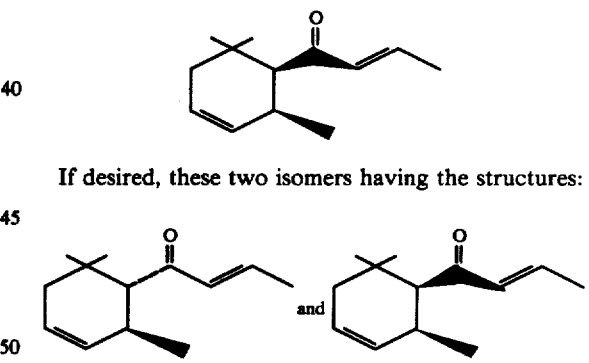

If desired, these two isomers having the structures:

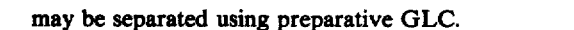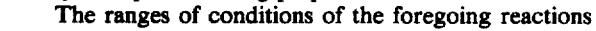

may be separated using preparative GLC.

The ranges of conditions of the foregoing reactions are the same as those specified by Ayyar, Cookson and Kagi in the paper entitled: "Synthesis of δ-Damascone [trans-1-(2,6,6-Trimethylcyclohex-3-enyl)but-2-en-1-one] and β-Damascenone[trans-1-(2,6,6-Trimethylcyclohexa-1,3-dienyl)but-2-en-1-one]", J. Chem.Soc., Perkins Trans. 1, 1975 (17) 1727–36 in setting forth the production of trans-1-(6,6-dimethylcyclohexa-1,3-dienyl)but-2-en-1-one (see page 1736 of Ayyar, et al). The ranges of conditions of the foregoing reactions are also exemplified in the examples infra.

When the compound trans, trans-Δ-damascone or the mixture containing a high proportion of trans, trans-Δ-damascone and less than 50% of cis, trans-Δ-damascone of our invention are used as food flavor adjuvants, the nature of the co-ingredients included with the trans, trans-Δ-damascone or composition containing a high proportion of trans, trans-Δ-damascone and less than 50% of cis, trans-Δ-damascone used in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to means the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the compound trans, trans-Δ-damascone or composition containing a high proportion of trans, trans-Δ-damascone and less than 50% cis, trans-Δ-damascone of our invention, and in addition, sweetening agents which may be sugars, including sucrose or dextrose and/or artifical sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizers compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate, texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include orgain acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl- 4-pentenal, 2-phenyl-2-hexenal, 2-phenyl-2-pentenal, furfural 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geranoil, 1-hexanal, 2-heptanol, trans-2-hexenol-1, cis-3-hexen-1-ol, 3-methyl-3-buten-1-ol, 1-pentanol, 1-penten3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimetyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha pinene; pyrazines such as 2,3-dimethylpyrazine, 2,5-dimethyl- pyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, assia oil, cinnamon bark oil, rose absolute, orris absolute, lemon essential oil, Bulgarian rose, yara yara and vanilla; lactones such as δ-nonalactone; sulfides e.g., methyl sulfide and other materials such as maltol, acetoin and acetals (e.g., 1,1-diethoxyethane, 1,1-mimethoxyethane and dimethoxymethane).

The specific flavoring adjuvant selected for use may be either solid or liquid depending upon the desired physical form of the ultimate product, i.e., foodstuff, whether simulated or natural, and should, in event, (i) be organoleptically compatible with the compound trans, trans-Δ-damascone or composition containing a high proportion of trans, trans-Δ-damascone and less than 50% of cis, trans-Δ-damascone of our invention by not covering or spoiling the organoleptic properties (aroma and/or taste) thereof; (ii) be non-reactive with the compound trans, trans-Δ-damascone or composition containing a high proportion of trans, trans-Δ-damasconeand less than 50% of cis, trans-Δ-damascone of our invention and (iii) be capable of providing an environment in which the compound trans, trans-Δ-damascone or composition containing a high proportion of trans, trans-Δ-damascone and less than 50% of cis, trans-Δ-damascone of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the trans, trans-Δ-damascone or composition containing a high proportion of trans, trans-Δ-damascone and less than 50% of cis, trans-Δ-damascone employed in a particular instance can very over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the compound trans, trans-Δ-damascone or composition containing a high proportion of trans, trans-Δ-damascone and less than 50% of cis, trans-Δ-damascone will, of course, substantially vitiate any possibility of obtaining the desired results while excess quantities prove needlessly costly and in extreme cases, may disrupt the flavor-aroma balance, thus providing self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the compound trans, trans-Δ-damascone or composition containing a high proportion of trans, trans-Δ-damascone and less than 50% of cis, trans-Δ-damascone ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the compound trans, trans-Δ-damascone or composition containing a high proportion of trans, trans-Δ-damascone and less than 50% of cis, trans-Δ-damascone is added to the foodstuff as an integral component of a flavoring composition, it is, of course, essential that the total quantity of flavoring composition employed be sufficient to yield an effective concentration of the trans, trans-Δ-damascone or composition containing a high proportion of trans, trans-Δ-damascone and less than 50% of cis, trans-Δ-damascone in the foodstuff product.

Food flavoring compositions prepared in accordance with the present invention preferably contain the compound trans, trans-Δ-damascone or composition containing a high proportion of trans, trans-Δ-damascone and less than 50% of cis, trans-Δ-damascone in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the compound trans, trans-Δ-damascone or composition containing a high proportion of trans, trans-Δ-damascone and less than 50% of cis, trans-Δ-damascone with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the compound trans, trans-Δ-damascone or composition containing a high proportion of trans, trans-Δ-damascone and less than 50% of cis, trans-Δ-damascone in a dry blender until the requisite degree of uniformity is achieved.

It is presently preferred to combine with the compound trans, trans-Δ-damascone or composition containing a high proportion of trans, trans-Δ-damascone and less than 50% of cis, trans-Δ-damascone of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
β-Damascone (1-crotonyl-2,2,6-trimethylcyclohex-1-ene);
β-Damascenone (1-crotonyl-2,2,6-trimethylcyclohexa-1,3-diene);
Beta-cyclohomocitral (2,2,6-trimethyl-cyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene prepared according to U.S. Application for Letters Pat. No. 461,703, filed on Apr. 17, 1974

The compound trans, trans-Δ-damascone or composition containing a high proportion of trans, trans-Δ-damascone and less than 50% of cis, trans-Δ-damascone and one or more auxiliary perfume ingredients, including for example, alcohols, aldehydes, ketones, terpinic hydrocarbons, nitriles, esters, lactones, natural essential oils and synthetic essential oils, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the compound trans, trans-Δ-damascone or composition containing a high proportion of trans, trans-Δ-damascone and less than 50% of cis, trans-Δ-damascone can be used to alter, modify or enhance the aroma characteristics of a perfume composition, for example, by utilizing or moderating the olfactory reaction contributed by another ingredient in the composition.

The amount of the trans, trans-Δ-damascone or composition containing a high proportion of trans, trans-Δ-damascone and less than 50% of cis, trans-Δ-damascone of our invention which will be effective in perfume compositions as well as in perfumed articles and colognes depends on many factors, including the other ingredients, their amounts and the effects which are desired. It has been found that perfume compositions containing as little as 0.01% of the trans, trans-Δ-damascone or composition containing a high proportion of trans, trans-Δ-damascone and less than 50% of cis, trans-Δ-damascone or even less (e.g., 0.005%) can be used to impart a rose, berry, apple, green and sweet floral note to soaps, cosmetics or other products. The amount employed can range up to 70% of the fragrance components and will depend on considerations of cost, nature of the end product, the effect desired on the finished product and the particular fragance sought.

The compound trans, trans-Δ-damascone or composition containing a high proportion of trans, trans-Δ-damascone and less than 50% of cis, trans-Δ-damascone of our invention is useful [taken alone or together with other ingredients in perfume compositions] as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 1% of the trans, trans-Δ-damascone or composition containing a high proportion of trans, trans-Δ-damascone and less than 50% of cis, trans-Δ-damascone will suffice to impart an intense floral note to rose formulations. Generally, no more than 3% of the trans, trans-Δ-damascone or composition containing a high proportion of trans, trans-Δ-damascone and less than 50% of cis, trans-Δ-damascone, based on the ultimate end product, is required in the perfume composition.

In addition, the perfume composition or fragrance composition of our invention can contain a vehicle, or carrier for the compound trans, trans-Δ-damascone or composition containing a high proportion of trans, trans-Δ-damascone and less than 50% of cis, trans-Δ-damascone. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the compound trans, trans-Δ-damascone or composition containing a high proportion of trans, trans-Δ-damascone and less than 50% of cis, trans-66-damascone of our invention can be utilized to alter, modify or enhance sensory properties, particularly organoleptic properties, such as flavor(s) and/or fragrance(s) of a wide variety of consumable materials.

Furthermore, the trans, trans-Δ-damascone or composition containing a high proportion of trans, trans-Δ-damascone and less than 50% of cis, trans-Δ-damascone of our invention are capable of supplying and/or potentiating certain flavor and aroma notes usually lacking in many tobacco flavors heretofore provided.

As used herein in regard to tobacco flavors, the terms "alter" and "modify" in their various forms means "supplying or imparting flavor character or note to otherwise bland tobacco, tobacco substituents, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives thereof, as well as methods of making the same which overcome specific problems heretofore encountered in which specific desired floral, musty, hay-tea-like, sweet and fruity aroma and taste nuances thereof, are created or enhanced and may be readily controlled and maintained at the desired uniform level regardless of variations in the tobacco components of the blend.

This invention further provides improved tobacco additives and methods whereby various floral, musty, hay-tea-like, sweet and fruity notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient the trans, trans-Δ-damascone or composition containing a high proportion of trans, trans-Δ-damascone and less than 50% of cis, trans-Δ-damascone of our invention.

In addition to the trans, trans-Δ-damascone or composition containing a high proportion of trans, trans-Δ-damascone and less than 50% of cis, trans-Δ-damacone of our invention, other flavoring and aroma additives may be added to the smoking tobacco materials or substitute therefor either separately or in mixture with the trans, trans-Δ-damascone or composition containing a high proportion of trans, trans-Δ-damascone and less than 50% of cis, trans-Δ-damascone as follows:

(i) Synthetic Materials:

Beta-ethyl-cinnamaldehyde;
Beta-cyclohomocitral;
Eugenol;
Dipentene;
Damascenone;
Damascone;
Maltol;
Ethyl Maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxy-ethyl)-decahydronaphthalene;
Dodecahydro-3a, 6,6,9a-tetramethylnaphtho[2,1,b]-furan;
4-Hydroxy hexanoic acid, gamma lactone; and
Polyisoprenoid hydrocarbons defined in Example V of U.S. Pat. No. 3,589,372 issued on June 29, 1971.

(ii) Natural Oils:

Celery seed Oil;
Coffee extract;
Bergamot oil;
Cocoa extract;
Nutmeg Oil;
Origanum Oil.

An aroma and flavoring concentrate containing the trans, trans-Δ-damascone or composition containing a high proportion of trans, trans-Δ-damascone and less than 50% of cis, trans-Δ-damascone and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the trans, trans-Δ-damascone or composition containing a high proportion of trans, trans-Δ-damascone and less than 50% of cis, trans-Δ-damascone to smoking tobacco material is between 250 ppm and 1,500 ppm (0.025%–0.15%) of the active ingredients to the smoking tobacco material. We have further found that satisfactory results are obtained if the proportion by weight of the sum total of the trans, trans-Δ-damascone or composition containing a high proportion of trans, trans-Δ-damascone and less than 50% of cis, trans-Δ-damascone used to flavoring material is between 2,500 and 15,000 ppm (0.25%–1.5%).

Any convenient method for incorporating the trans, trans-Δ-damascone or composition containing a high proportion of trans, trans-Δ-damascone and less than 50% of cis, trans-Δ-damascone in the tobacco product may be employed. Thus, the trans, trans-Δ-damascone or composition containing a high proportion of trans, trans-Δ-damascone and less than 50% of cis, trans-Δ-damascone taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of the trans, trans-Δ-damascone or composition containing a high proportion of trans, trans-Δ-damascone and less than 50% of cis, trans-Δ-damascone taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the trans, trans-Δ-damascone or composition containing a high proportion of trans, trans-Δ-damascone and les than 50% of cis, trans-Δ-damascone in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of the trans, trans-Δ-damascone or composition containing a high proportion of trans, trans-Δ-damascone and less than 50% of cis, trans-Δ-damascone in an amount to provide a tobacco composition containing 800 ppm by weight of the trans, trans-Δ-damascone or composition containing a high proportion of trans, trans-Δ-damascone and less than 50% of cis, trans-Δ-damascone on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and side streams when the cigarette is smoked. This aroma is described as having floral, musty, hay-tea-like, sweet and fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, the trans, trans-Δ-damascone or composition containing a high proportion of trans, trans-Δ-damascone and less than 50% of cis, trans-Δ-damascone of our invention can be incorporated with materials such as filter tip materials, seam paste, packaging materials and the like which are used along with tobacco to form a product adapted for smoking. Furthermore, the trans, trans-Δ-damascone or composition containing a high proportion of trans, trans-Δ-damascone and less than 50% of cis, trans-Δ-damascone can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following Example I serves to illustrate the prior art. The following Examples II-IX serve to illustrate our invention and the invention is to be considered restricted thereto only as indicated in the appended claims.

All parts and percentages given herein are by weight unless otherwise specified.

EXAMPLE I

PREPARATION OF COMPOSITION CONTAINING HIGH PROPORTION OF CIS, TRANS-Δ-DAMASCONE (ACCORDING TO AYYAR, ET AL)

Reaction Sequence:

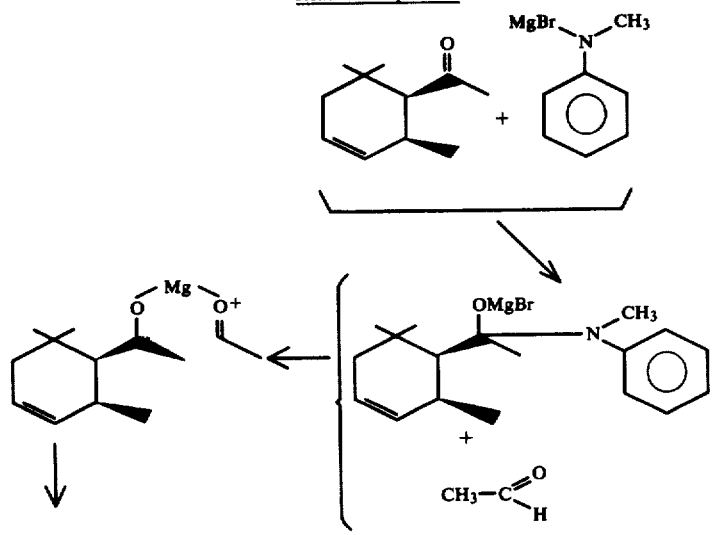

Reaction Sequence:

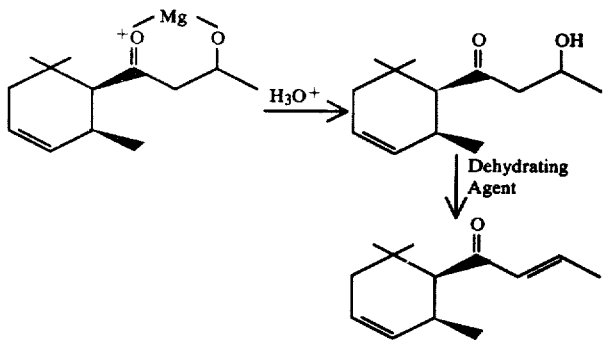

Procedure

Part A: Preparation of Mixture of Major Proportion of Trans-4-Acetyl-3,5,5-Trimethylcyclohexene and Low Proportion of Cis Isomer

To powdered anhydrous aluminum chloride (13.7 g, 0.10 mol) under nitrogen is added dry dichloromethane (30 ml). Mesityl oxide (20.0 g, 0.20 mol) in dichloromethane (75 ml) is then added with stirring over 30 minutes and the mixture is heated under reflux for 1 hour. Penta-1,3-diene (mixture of isomers) (70.0 g, 1.03 mol) in dichloromethane (300 ml) is added dropwise over 6 hours. The mixture is then stirred overnight at room temperature. Liquid paraffin (100 ml) and 10% hydrochloric acid (200 ml) is added and the mixture is steam distilled for 3 hours. The steam distillate is extracted with ether (5×75 ml) and the product worked up as usual. The residue is distilled to give a liquid, b.p. 52°–54° at 1 mm Hg (15.0 g, 0.09 mol, 45%), shown by GLC [column (A), 120° C.] to consist of two components in the proportions ca. 13:87 in order of increasing retention time. These were separated by preparative GLC [column (B), 130° C.]: trans-4-acetyl-3,5,5-trimethylcyclohexene (6) (Found: C, 79.6; H, 10.75. $C_{11}H_{18}O$ requires C, 79.5; H, 10.85%); m/e 166 (M+, 33%), 123 (100), 109 (39), 107 (33), 81 (39), 69 (33), 67 (27), 55 (27), 43 (82) and 41 (50); τ9.17–8.86 (9H, 4 overlapping lines, 3- and 5-Me), 8.60–8.04 (2H, m, 6-$H_2$), 7.87 (3H, s, Ac), 7.90–7.30 (2H, m with br s overlapping, 3- and 4-H), and 4.54 br (2H, s, 1- and 2-H); $\nu_{max}$. (film) 1 710 (Ac) and 695 $cm^{-1}$ (cis—CH=CH); cis-4-acetyl-3,5,5-trimethylcyclohexene (5) (Found: C, 79.55; H, 10.8%); m/e 166 (M+, 4%), 138 (39), 123 (95), 109 (11), 107 (23), 81 (12), 69 (8), 67 (9), 55 (12), 53 (11), 43 (100) and 41 (23); τ9.18–8.89 (9H, 3 overlapping lines, 3- and 5-Me), 8.68–8.18 (2H, m, 6-$H_2$), 7.97 (3H, s, Ac), 7.70–7.30 (2H, m, 4- and 3-H), and 4.86–4.16 (2H, m, 1- and 2-H); $\nu_{max}$. (film) 1 710 (Ac), and 1 692 and 710 $cm^{-1}$ (cis-CH=CH).

Part B: Preparation of Cis, Trans-Δ-Damascone

The resulting mixture of 4-acetyl-3,5,5-trimethylcyclohexenes (mixture of trans and cis stereoisomers with the trans isomer predominating) are treated with acetaldehyde and the resultant mixture is dehydrated according to the following procedure:

To a solution of ethyl magnesium bromide [from magnesium turnings, 0.92 grams, and ethyl bromide, 4.20 grams, in dry ether, 10 ml] N-methyl aniline, 4.1 grams, in dry benzene, 5 ml, is added with stirring and cooling. The 4-acetyl-3,5,5-trimethylcyclohexene isomer mixture produced in Part A, 5.00 grams, in benzene, 5 ml, is added to the cooled mixture which is stirred at room temperature for 30 minutes and then cooled while acetaldehyde, 1.90 grams in benzene, 10 ml, is added during the 20 minute period. The mixture is stirred for a further 30 minutes at 0° C. and then poured into ice (20 grams) and 10% hydrochloric acid (50 ml). The mixture is extracted with petroleum (5×50 ml) and the combined extracts are washed with 10% hydrochloric acid (5×50 ml) and worked up. The residue (6.00 g) is diluted with dry benzene (100 ml) and paratoluenesulfonic acid (0.20 grams) is added. The mixture is heated under reflux and the water formed is removed azeotropically in a Dean Stark apparatus. Distillation of the dehydrated product under reduced pressure yields a mixture of the isomers of Δ-damascone, a high proportion of cis, trans-Δ-damascone and a low proportion of trans, trans-Δ-damascone. B.p. 65°–67° at 0.6 mm Hg (2.8 g, 15 mmol, 50%) (Found: C, 81.2; H, 10.3. $C_{13}H_{20}O$ requires C, 81.25; H, 10.4%); m/e 192 (M+, 48%), 177 (17), 137 (13), 123 (56), 109 (21), 107 (19), 91 (15), 93 (15), 81 (36), 69 (100), 55 (17) and 41 (52); τ9.12 and 9.03 (9H, 2s, 6-$Me_2$ overlapping the d due to 2-Me), 8.16 (3H, dd, J 6.5 and 1 Hz, —C=C—$CH_3$), 8.40-7.22 (4H, m, ring 5-$H_2$, 1-H, and 2-H), 4.72-4.22 (2H, m, ring 3- and 4-H), 3.93 (1H, dq, J 16 and 1 Hz, —CO—CH=C), and 3.29 (1H, dq, J 6.5 and 16 Hz, —C=CH—$CH_3$); $\nu_{max}$. (film) 1 695, 1 665, 1 630 (—CH=C—CO—), and 970 $cm^{-1}$ (trans-CH=CH); $\lambda_{max}$. (cyclohexane) 223 nm (ε10 100).

The Mass Spectral analysis is as follows:

| m/e | Relative Intensity |
| --- | --- |
| 41 | $10^6$ |
| 69 | $100^0$ |
| 81 | $20^4$ |
| 83 | 7 |
| 107 | 8 |
| 108 | 7 |
| 109 | $13^5$ |
| 123 | $34^2$ |
| 177 | 7 |
| M192 | $20^3$ |

Figure 2:
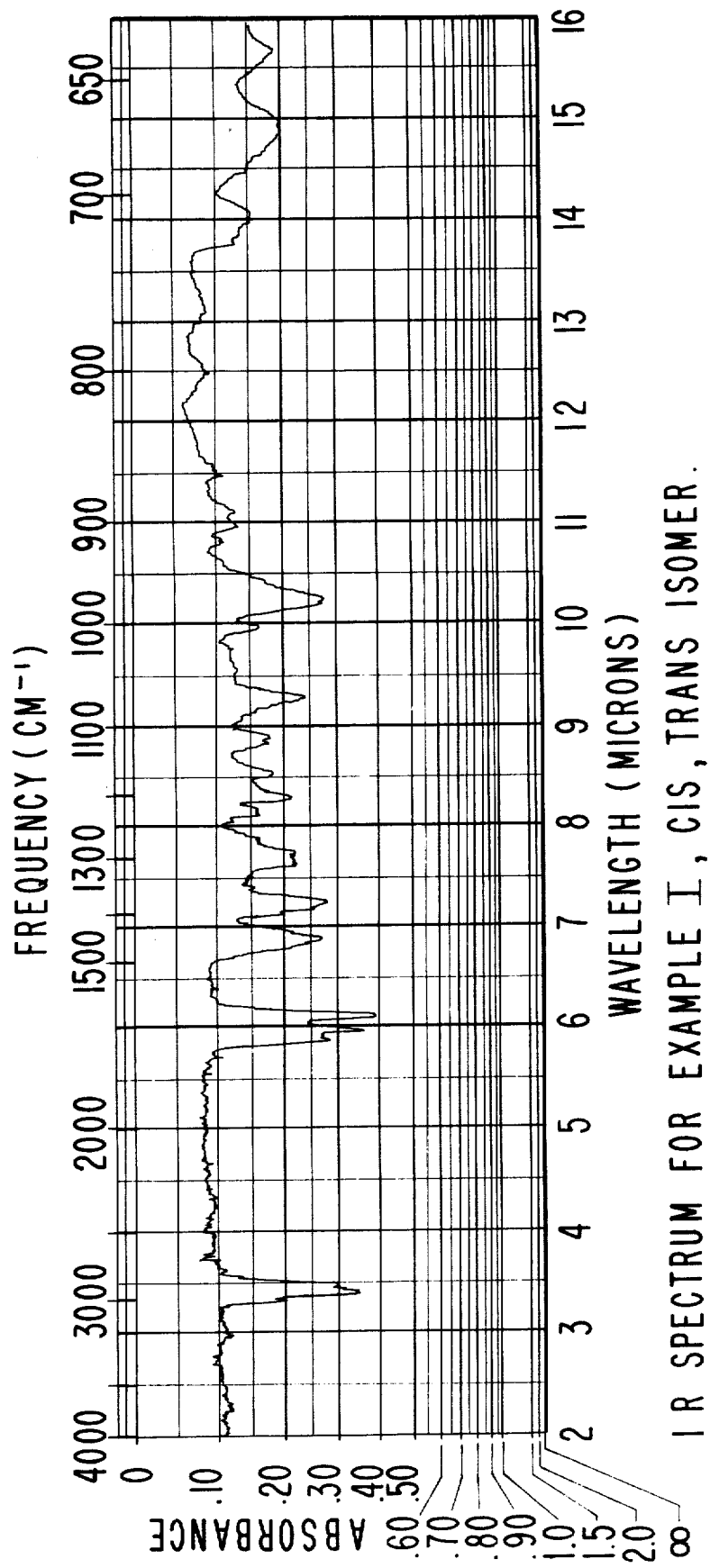
FIG. 2 represents the Infrared spectrum for cis, trans-Δ-damascone produced according to the process of Example I.

FIG. 1 sets forth the NMR spectrum of cis, trans-Δ-damascone. FIG. 2 sets forth the Infrared spectrum of cis, trans-Δ-damascone.

EXAMPLE II

PREPARATION OF TRANS, TRANS-Δ-DAMASCONE

Reaction Sequence:

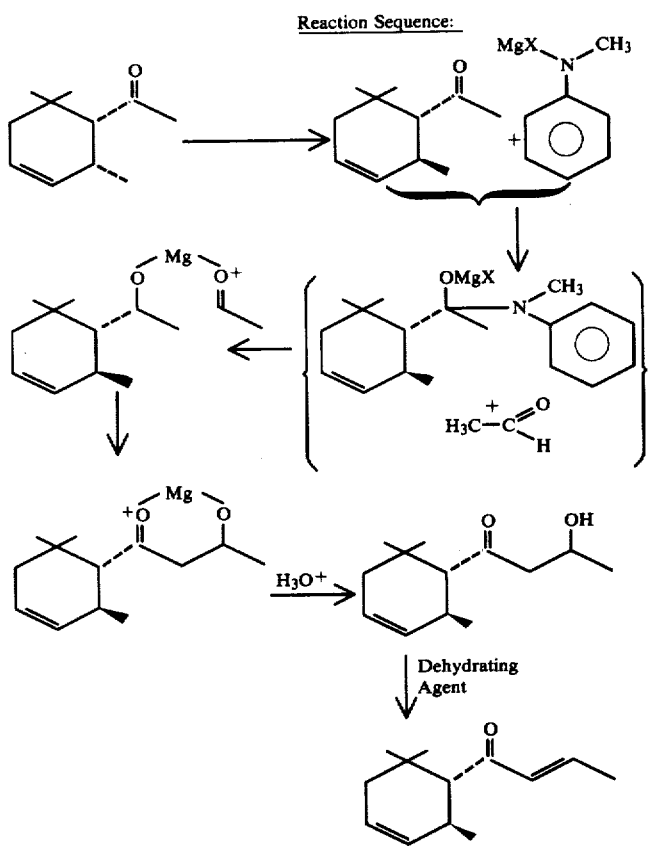

Procedure

Part A: Preparation of 1-α-Acetyl-2-β, 6,6-Trimethyl-3-Cyclohexene

To a 1 liter receiver equipped with magnetic stirrer, reflux condenser, heating mantle and thermometer, is added 34.6 g 1-α-acetyl-2-β, 6,6-trimethyl-cis-3-cyclohexene, 500 ml ethanol (food grade) and 10 g potassium hydroxide. This mixture is then refluxed with stirring for 25 hours. The alcohol is then removed by rotary evaporator and the residue dissolved in ether (150 ml) and washed five times with saturated sodium chloride solution (25 ml portion) and is then dried over magnesium sulfate. 33.7 g of the resulting crude product is distilled to give 11 fractions, all of which contained ≈80% of product, 1-α-acetyl-2-β, 6,6,-trimethyl-3-cyclohexene having the structure:

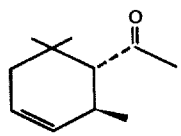

Yield of conversion: 74%.

Part B: Preparation of Trans, Trans-Δ-Damascone

To a 500 ml three necked reaction flask equipped with magnetic stirrer, addition funnel, thermometer, reflux condenser, nitrogen purge, heating mantle and isopropanol cooling bath, is added:

6 g magnesium turnings
50 ml anhydrous ether

To the magnesium turnings, via addition funnel, is added 26 g of ethyl bromide in 50 ml of dry ether. After addition the mixture is refluxed for ½ hour. The mixture is then cooled to 0° C. and 25 g of N-methylaniline in 30 ml of dry benzene is added over a ½ hour period. 1-α-Acetyl-2-β, 6,6-trimethyl-3-cyclohexene (30 g) in 30 ml of benzene is added dropwise over a 45 minute period at 0°-5° C. and is then warmed up to room temperature (24° C.) and stirred for ½ hour. The mixture is then cooled again to 0° C. while redistilled acetaldehyde (12 g) in 50 ml of benzene is added over a 30 minute period. The mixture is then stirred for 1 hour at 0° C. and then poured into 200 g of ice containing 100 ml 10% hydrochloric acid. The mixture is then extracted five times with petroleum ether (50 ml portion) and the extracts are combined and washed two times with 10% hydrochloric acid (50 ml) and five times with saturated sodium chloride (50 ml) and dried over MgSO₄. After the solvent is evaporated, 37.1 g of crude material resulted.

The crude keto alcohol (37.1 g) in 500 ml of anhydrous benzene is added to a 1 liter receiver containing 1 gram of paratoluenesulfonic acid. This mixture is refluxed for 8 hours while 3 mls of water is removed via a Bidwell trap. The crude material in benzene solution is then washed three times with 10% Na₂CO₃ (100 ml portions) and four times with saturated NaCl solution (100 ml portions), dried and the solvent removed. This material is then distilled on a micro-Vigreux column to yield 13 fractions. Fractions 4–13 (20.1 g) are combined for column chromatography to remove the starting material, α-acetyl-2-β, 6,6-trimethyl-3-cyclohexenyl. This material is then eluted on a glass chromatography column containing 200 g of SiO₂ (5% water deactivated). The following column eluates are discarded: 1% Fraction 1 (0.5 g), 1% Fraction 2 (0.5 g), 1% Fraction 3 (1.3 g), 1% Fraction 4 (0.7 g), 1% Fraction 5 (1.5 g), 2% (0.8 g), Fraction 5 0.9 g. Fractions 16 (0.5 g), 17 (0.5 g) and 18 (0.5 g) of 1% ether eluates are combined and kept (contains 50% of cis, trans and trans, trans isomer). Fractions 6–15 of 1% ether eluate are combined and redistilled to give 10 fractions. Spectral tests confirm that the product having the structure:

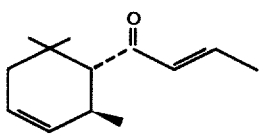

and a purity of 93% (the other 7% consists of 5% cis, trans isomer and 2% unidentified product) is made.

The Mass Spectral analysis for trans, trans-Δ-damascone is as follows:

| m/e | Relative Intensity |
|---|---|
| 41 | 14$^5$ |
| 69 | 100$^1$ |
| 70 | 9 |
| 81 | 22$^4$ |
| 107 | 11$^6$ |
| 109 | 9 |
| 121 | 8 |
| 122 | 8 |
| 123 | 38$^2$ |
| M192 | 31$^3$ |

Figure 3:
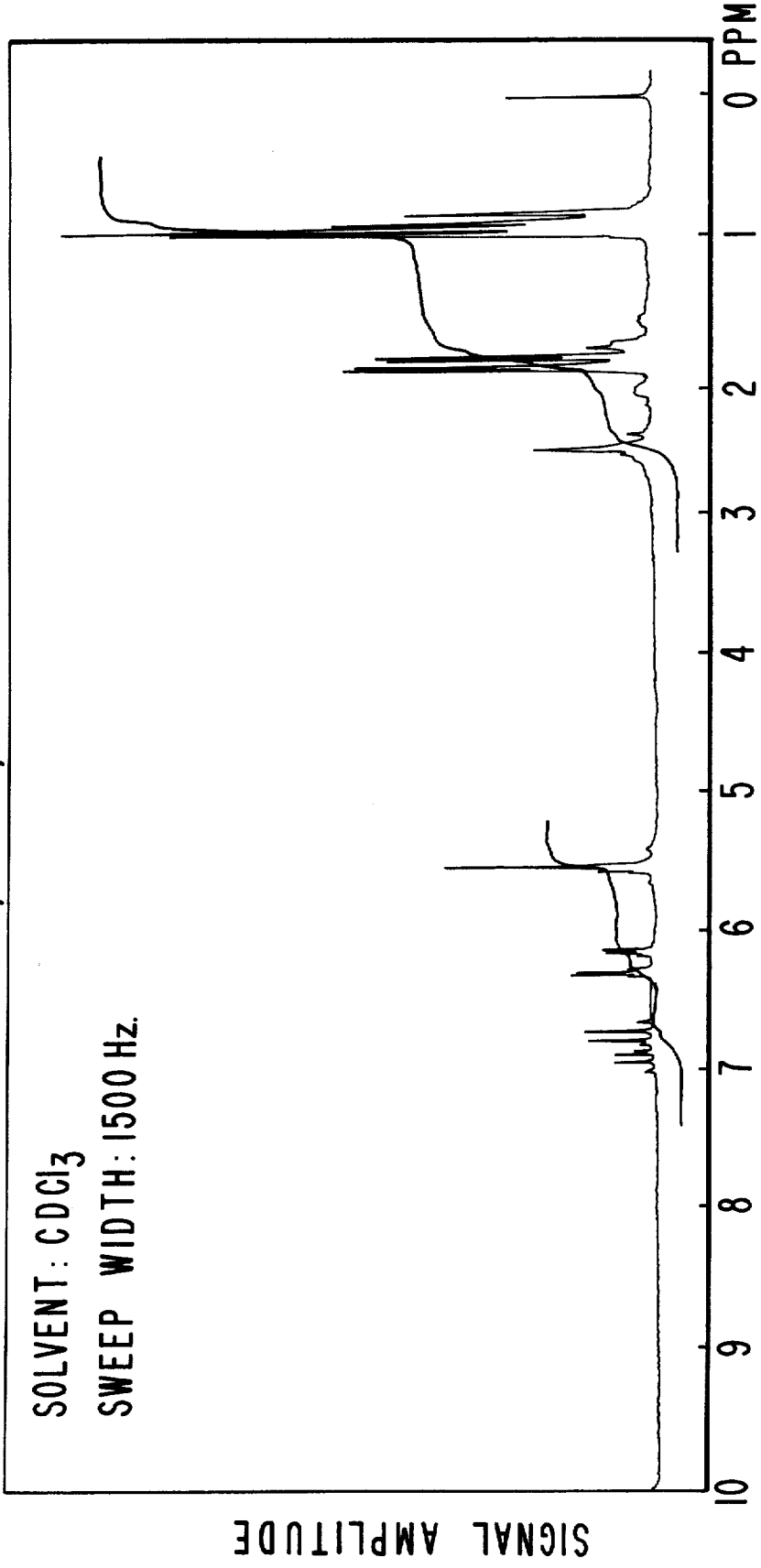
FIG. 3 represents the NMR spectrum for trans, trans-Δ-damascone produced according to the process of Example II.
Figure 4:
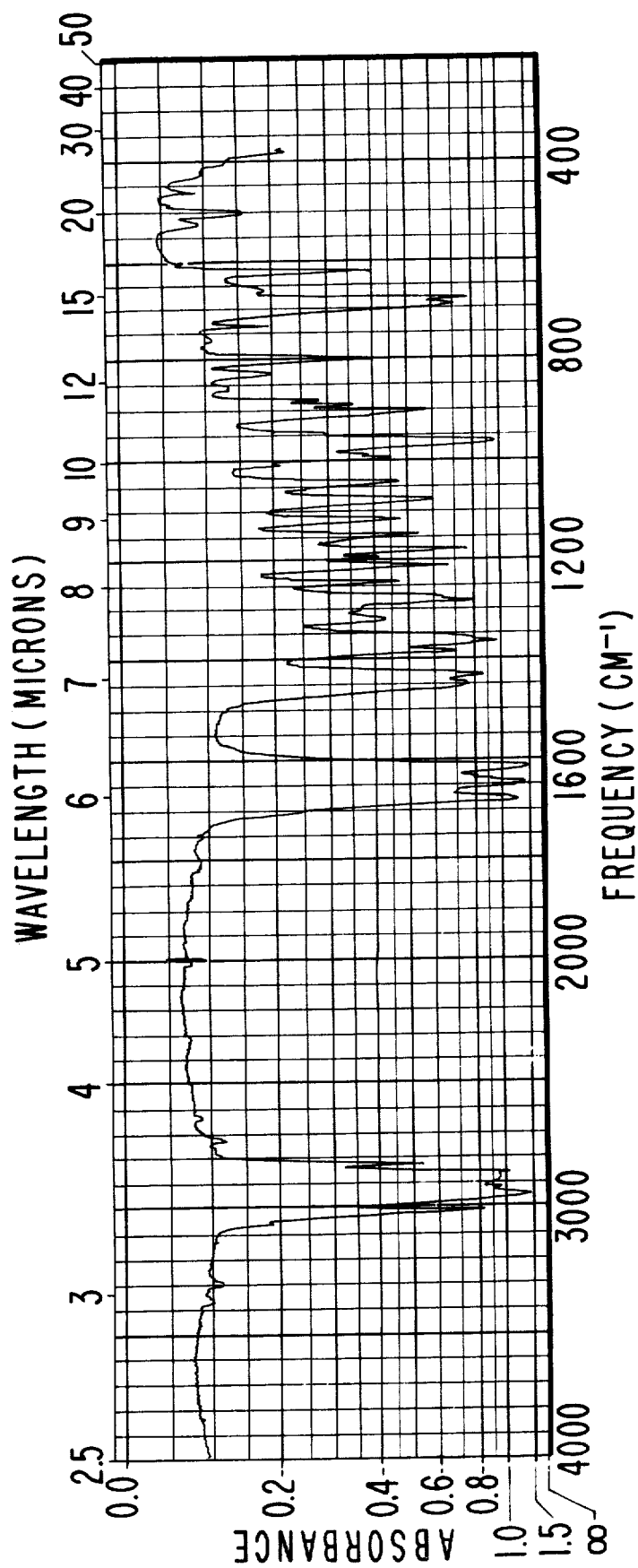
FIG. 4 represents the Infrared spectrum for trans, trans-Δ-damascone produced according to Example II.

FIG. 3 represents the NMR spectrum for trans, trans-Δ-damascone, Fraction 6. FIG. 4 represents the Infrared spectrum for trans, trans-Δ-damascone, Fraction 6.

EXAMPLE III

COMPARISON OF PERFUME COMPOSITIONS CONTAINING PRODUCT OF EXAMPLE I CONTAINING A HIGH PROPORTION OF CIS, TRANS-Δ-DAMASCONE AND COMPOSITION OF EXAMPLE II CONTAINING A HIGH PROPORTION OF TRANS, TRANS-Δ-DAMASCONE

The trans, trans-Δ-damascone has a fine tobacco-rose, appley, berry note. The cis, trans-Δ-damascone isomer, on the other hand, is floral but with a camphoraceous, mintyness which renders it less desirable as a perfumery material. This difference is seen quite readily when the above-mentioned Δ-damascones are compared in an actual fragrance composition, wherein 3% of a 10% solution in diethyl phthalate is used. The following rose perfume demonstrates the effect:

| Ingredient | I | II | III |
|---|---|---|---|
| Rhodinol | 250 | 250 | 250 |
| Phenylethyl alcohol | 195 | 195 | 195 |
| Alpha methyl ionone | 80 | 80 | 80 |
| Linalyl acetate | 60 | 60 | 60 |
| Cis-3-hexenyl acetate | 5 | 5 | 5 |
| Jasmine absolute | 10 | 10 | 10 |
| Cinnamic alcohol | 20 | 20 | 20 |

-continued

| Ingredient | I | II | III |
|---|---|---|---|
| Rhodinyl acetate | 60 | 60 | 60 |
| Cyclohexyl ethyl alcohol | 20 | 20 | 20 |
| Geraniol | 130 | 130 | 130 |
| Geranyl acetate | 80 | 80 | 80 |
| Paraisopropyl cyclohexanol | 60 | 60 | 60 |
| Diethyl phthalate | 30 | — | — |
| Cis, trans-Δ-damascone (10% in diethyl phthalate) | — | 30 | — |
| Trans, trans-Δ-damascone (10% in diethyl phthalate) | — | — | 30 |
| Total | 1000 | 1000 | 1000 |

The trans, trans-Δ-damascone lends a sweet floral rose note to the fragrance composition. On the other hand, the cis, trans isomer could be said to have ruined the perfume, giving it a very rough musty topnote which is not desirable in perfume compositions. The undesirable character of the cis, trans isomer is enhanced by its use in the fragrance. This effect is not expected.

The desirable trans, trans-Δ-damascone may be used in perfume compositions at from 0.05 up to 25%. Larger amounts may be used for special effects.

EXAMPLE IV

COMPARISON OF SOAPS CONTAINING PRODUCT OF EXAMPLE I, CONTAINING A HIGH PROPORTION OF CIS, TRANS-Δ-DAMASCONE VERSUS PRODUCT OF EXAMPLE II CONTAINING A HIGH PROPORTION OF TRANS, TRANS-Δ-DAMASCONE

Both the trans, trans and the cis, trans were incorporated into soap (LVU-1) at 0.1% by weight. After two weeks in the oven at 90° F., both isomers showed no visual effect from the heat. On the other hand, the odor of the trans, trans was far superior to the cis, trans which had a harsh camphoraceous topnote and may be considered unsuitable for soap perfumery.

EXAMPLE V

PREPARATION OF A COSMETIC POWDER COMPOSITION

A cosmetic powder is prepared by mixing in a ball mill, 100 g of talcum powder with 0.25 g of the trans, trans-Δ-damascone produced according to Example II. It has an excellent rose, berry, apple, green and sweet floral note.

EXAMPLE VI

PERFUMED LIQUID DETERGENT

Concentrated liquid detergents with rose, berry, apple, green and sweet floral notes (which detergents are produced from Lysine salt of n-dodecyl benzene sulfonic acid as more specifically described in U.S. Pat. No. 3,948,818, issued on Apr. 6, 1976) are prepared containing the trans, trans-Δ-damascone prepared according to Example II. They are prepared by adding and homogeneously mixing the appropriate quantity of the trans, trans-Δ-damascone in the liquid detergent. The detergents all possess a rose, berry, apple, green and sweet floral note, the intensity increasing with greater concentrations of the trans, trans-Δ-damascone.

EXAMPLE VII

PREPARATION OF A COLOGNE AND HANDKERCHIEF PERFUME

The trans, trans-Δ-damascone prepared according to Example II is incorporated in a cologne at a concentration of 2.5% in 85% aqueous ethanol; and into a handkerchief perfume at a concentration of 20% (in 95% aqueous ethanol). A distinct and definite rose, berry, apple, green and sweet floral note is imparted to the cologne and to the handkerchief perfume.

EXAMPLE VIII

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

Trans, trans-Δ-damascone is added to half of the above formulation at the rate of 0.2%. The formulation with the trans, trans-Δ-damascone is compared with the formulation without the trans, trans-Δ-damascone at the rate of 0.01% (100 ppm) in water and evaluated by a bench panel.

The flavor containing the trans, trans-Δ-damascone is found to have a substantially more pleasant and better raspberry aroma. It is the unanimous opinion of the bench panel that the chemical, trans, trans-Δ-damascone rounds the flavor out and contributes to a very natural fresh aroma and taste as found in full ripe raspberries. Accordingly, the flavor with the addition of the trans, trans-Δ-damascone is considered as substantially better than the flavor without trans, trans-Δ-damascone.

EXAMPLE IX

TOBACCO FORMULATION

A tobacco mixture is produced by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the mixture produced according to Example II of trans, trans-Δ-damascone. The control cigarettes not containing the mixture of trans, trans-Δ-damascone produced according to the process of Example II and the experimental cigarettes which contain the mixture of trans, trans-Δ-damascone produced according to Example II are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, musty, hay-tea-like, sweet and fruity aroma and taste nuances.

The tobacco smoke flavor of the experimental cigarettes, prior to smoking, has floral, musty, hay-tea-like, sweet and fruity notes. All cigarettes are evaluated for smoke flavor with a 20 mm cellulose acetate filter.

EXAMPLE X

LARGE SCALE PREPARATION OF TRANS, TRANS-Δ-DAMASCONE

Reaction Sequence:

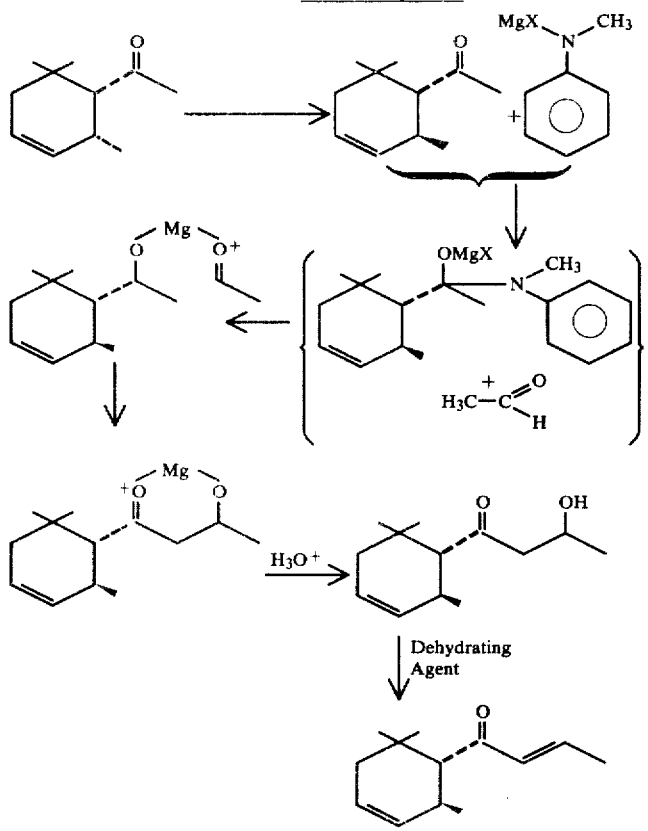

Procedure:

Part A: Preparation of 1-α-Acetyl-2-β, 6,6-Trimethyl-3-Cyclohexene

To a 3 liter glass reactor equipped with magnetic stirrer, reflux condenser, heating mantle and thermometer, is added 1056 g anhydrous CH₃OH. 44 Grams of sodium metal is then added slowly to the methanol while maintaining the temperature at 25° C. 1085 Grams of 1-α-acetyl-2-β, 6,6-trimethyl-cis-3-cyclohexene is then added to the reaction mixture. This mixture is then refluxed with stirring for 24 hours. 120 Grams of acetic acid is then added to the reaction mass. The reaction mass is then washed with one equal volume of water and one liter of saturated sodium chloride solution. Crude weight is 1040 grams. The resulting product is rushed over in a 1 foot saddle column, yielding the following fractions:

| Fraction No. | Vapor Temperature | Liquid Temperature | Vacuum mm Hg | Weight of Fraction |
|---|---|---|---|---|
| 1 | 38–81 | 88–94 | 9.0 | 42.0 |
| 2 | 85 | 100 | 9.0 | 244.0 |
| 3 | 86 | 100 | 9.0 | 99.0 |
| 4 | 86 | 102 | 9.0 | 114.0 |
| 5 | 87 | 102 | 9.0 | 107.0 |
| 6 | 90 | 110 | 11.0 | 96.0 |
| 7 | 90 | 110 | 11.0 | 99.0 |
| 8 | 97 | 120 | 11.0 | 88.0 |
| 9 | 120 | 135 | 11.0 | — |

The fractions contain the product 1-α-acetyl-2-β, 6,6-trimethyl-3-cyclohexene having the structure:

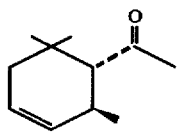

Part B: Preparation of Trans, Trans-Δ-Damascone

To a 1 liter three necked reaction flask equipped with magnetic stirrer, addition funnel, thermometer, reflux condenser, nitrogen purge, heating mantle and isopropanol cooling bath, is added 365 ml (1.1 moles) of methyl magnesium chloride. 168 Grams (1.1 moles) of N-methyl aniline is then slowly added to the methyl magnesium chloride while maintaining the temperature at 30° C. Following the addition of the N-methyl aniline, 75 ml additional CH₃MgCl (methyl magnesium chloride) is added. Over a period of 15 minutes, 1-α-acetyl-2-β, 6,6-trimethyl-3-cyclohexene (200 grams/1.0 moles) is added to the reaction mass while maintaining the temperature at 30°–34° C. with cooling. Following the addition of 1-α-acetyl-2-β, 6,6-trimethyl-3-cyclohexene, the reaction mass is cooled to 0° to −5° C.

and while maintaining the reaction mass temperature at 0° to −5° C., 49 grams (1.1 moles) of acetaldehyde dissolved in 120 ml of toluene is added to the reaction mass. Following the acetaldehyde addition, 10% aqueous hydrochloric acid is aadded and the aqueous layer is separated from the organic layer. The organic layer is stripped of solvent at 35° C. under vacuum yielding a crude material weighing 240 grams.

To the 240 grams of the resulting intermediate, is added 150 ml acetic anhydride and 25 grams of sodium acetate in a 500 ml reaction flask. The resulting reaction mixture is heated to 100°–115° C. over a period of 3 hours. At the end of the 3 hour heating period the reaction mass is cooled to 80° C. and an equal volume of water is added to destroy the excess acetic anhydride. The organic layer is separated from the aqueous layer and the organic layer is washed with an equal volume of water and an equal volume of saturated sodium bicarbonate. The organic layer is then stripped of solvent and distilled under the following conditions:

| Fraction No. | Vapor Temperature | Liquid Temperature | Vacuum mm Hg | Reflux Ratio | Weight of Fraction |
|---|---|---|---|---|---|
| 1 | 51–53 | 83–99 | 2.2–2.7 | 4:1 | 15.2 |
| 2 | 53 | 100 | 1.8 | 4:1 | 12.5 |
| 3 | 72 | 102 | 1.7 | 4:1 | 11.3 |
| 4 | 77–85 | 101–104 | 2.5–2.6 | 4:1 | 7.4 |
| 5 | 87 | 105 | 2.5 | 4:1 | 21.3 |
| 6 | 91 | 108 | 3.9 | 1:1 | 27.3 |
| 7 | 87 | 110 | 3.1 | 1:1 | 26.5 |
| 8 | 87 | 119 | 3.1 | 1:1 | 24.7 |
| 9 | 87 | 125 | 3 | 1:1 | 11.02 |
| 10 | 88 | 135 | 3 | 1:1 | 4.3 |
| 11 | 81 | 250 | 3 | 1:1 | 8.2 | after adding to the mixture to be distilled 44.7 grams of "Primol ®" and 0.4 grams of "Ionox ®". Spectral tests confirm that the resulting product has the structure:

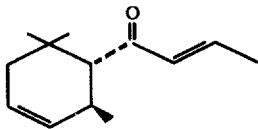

The Mass Spectral analysis for trans, trans-Δ-damascone is as follows:

| m/e | Relative Intensity |
|---|---|
| 41 | 14[5] |
| 69 | 100[1] |
| 70 | 9 |
| 81 | 22[4] |
| 107 | 11[6] |
| 109 | 9 |
| 121 | 8 |
| 122 | 8 |
| 123 | 38[2] |
| M192 | 31[3] |

FIG. 3 represents the NMR spectrum for trans, trans-Δ-damascone, Fraction 6. FIG. 4 represents the Infrared spectrum for trans, trans-Δ-damascone, Fraction 6.

EXAMPLE XI

PREPARATION OF A COSMETIC POWDER COMPOSITION

A cosmetic powder is prepared by mixing in a ball mill, 100 g of talcum powder with 0.25 g of the trans, trans-Δ-damascone produced according to Example X. It has an excellent rose, berry, apple, green and sweet floral note.

EXAMPLE XII

PERFUMED LIQUID DETERGENT

Concentrated liquid detergents with rose, berry, apple, green and sweet floral notes (which detergents are produced from Lysine salt of n-dodecyl benzene sulfonic acid as more specifically described in U.S. Pat. No. 3,948,818, issued on Apr. 6, 1976) are prepared containing the trans, trans-Δ-damascone prepared according to Example X. They are prepared by adding and homogeneously mixing the appropriate quantity of the trans, trans-Δ-damascone in the liquid detergent. The detergents all possess a rose, berry, apple, green and sweet floral note, the intensity increasing with greater concentrations of the trans, trans-Δ-damascone.

EXAMPLE XIII

PREPARATION OF A COLOGNE AND HANDKERCHIEF PERFUME

The trans, trans-Δ-damascone prepared according to Example X is incorporated in a cologne at a concentration of 2.5% in 85% aqueous ethanol; and into a handkerchief perfume at a concentration of 20% (in 95% aqueous ethanol). A distinct and definite rose, berry, apple, green and sweet floral note is imparted to the cologne and to the handkerchief perfume.

EXAMPLE XIV

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

Trans, trans-Δ-damascone produced according to Example X is added to half of the above formulation at the rate of 0.2%. The formulation with the trans, trans-Δ-damascone is compared with the formulation without the trans, trans-Δ-damascone at the rate of 0.01% (100 ppm) in water and evaluated by a bench panel.

The flavor containing the trans, trans-Δ-damascone is found to have a substantially more pleasant and better raspberry aroma. It is the unanimous opinion of the bench panel that the chemical, trans, trans-Δ-damascone rounds the flavor out and contributes to a very natural fresh aroma and taste as found in full ripe raspberries. Accordingly, the flavor with the addition of the trans, trans-Δ-damascone is considered as substantially better than the flavor without trans, trans-Δ-damascone.

EXAMPLE XV

TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the mixture produced according to Example X of trans, trans-Δ-damascone. The control cigarettes not containing the mixture of trans, trans-Δ-damascone produced according to the process of Example X and the experimental cigarettes which contain the mixture of trans, trans-Δ-damascone produced according to Example II are evaluated by paired comparison and the results are as follows:

The experimental cigarettes are found to have more body in tobacco smoke flavor and a fuller body sensation. The tobacco-like notes are enhanced and the flavor of the tabacco on smoking is more aromatic with floral, musty, hay-tea-like, sweet and fruity aroma and taste nuances.

The tobacco smoke flavor of the experimental cigarettes, prior to smoking, has floral, musty, hay-tea-like, sweet and fruity notes. All cigarettes are evaluated for smoke flavor with a 20 mm cellulose acetate filter.

What is claimed is:

1. A process for augmenting or enhancing the aroma and taste of a smoking tobacco comprising adding to said tobacco an organoloptic property modifying quantity of a composition of matter consisting essentially of 80 to 85 percent of a synthetically produced trans, trans-Δ-damascone and 20–15 percent of a synthetically produced cis, trans-Δ-damascone.

2. A process for augmenting or enhancing the aroma and taste of a smoking tobacco comprising adding to said smoking tobacco in an organoleptic property modifying quantity, a product produced according to the process of (i) reacting 1-α-acetyl-2-α, 6,6-trimethyl-3-cyclohexene with strong base in aqueous ethanol at reflux thereby producing 1-α-acetyl-2-β, 6,6-trimethyl-3-cyclohexene; (ii) reacting the 1-α-acetyl-2-β, 6,6-trimethyl-3-cyclohexene with n-methyl aniline Grignard thereby forming a first organometallic compound; (iii) reacting said first organometallic compound with acetaldehyde thereby forming a second organometallic compound; (iv) reacting said second organometallic compound with acid in order to hydrolyze said second organometallic compound thereby forming a hydroxy ketone having the structure:

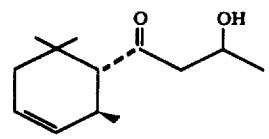

in admixture with other compounds; (v) dehydrating said hydroxy ketone in admixture with other compounds thereby forming a mixture having a major proportion of trans, trans-Δ-damascone having the structure:

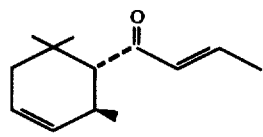

in admixture with cis, trans-Δ-damascone having the structure:

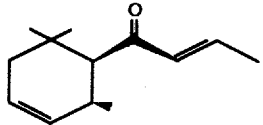

and in admixture with other compounds wherein said mixture contains 80 to 85 percent of the trans, trans-Δ-damascone and 20 to 15 percent of the cis, trans-Δ-damascone.

3. A smoking tobacco product comprising (i) smoking tobacco and (ii) intimately mixed with said smoking tobacco a composition suitable for augmenting or enhancing the organoleptic properties of said smoking tobacco which composition consists essentially of 80 to 85 percent of a synthetically produced trans, trans-Δ-damascone and 20–15 percent of a synthetically produced cis, trans-Δ-damascone.

4. The composition of claim 3 wherein the composition containing said synthetically produced trans, trans-Δ-damascone is added to the smoking tobacco in an amount between 250 ppm and 1,500 ppm.

5. A process of augmenting or enhancing the aroma and taste of a smoking tobacco comprising adding to said tobacco an organoleptic property modifying quantity of a composition matter consisting essentially of a substantially pure synthetically produced trans, trans-Δ-damascone.

* * * * *